United States Patent
Jordan et al.

(10) Patent No.: US 7,314,443 B2
(45) Date of Patent: Jan. 1, 2008

(54) IMPLANTABLE DEVICE

(75) Inventors: Alain Jordan, Lausanne (CH);
Jean-Charles Montavon, Lausanne (CH)

(73) Assignee: Allergan Medical S.A., Lausanne (CH)

( * ) Notice: Subject to any disclaimer, the term of this patent is extended or adjusted under 35 U.S.C. 154(b) by 72 days.

(21) Appl. No.: 10/506,790

(22) PCT Filed: Mar. 6, 2003

(86) PCT No.: PCT/EP03/02324

§ 371 (c)(1),
(2), (4) Date: Sep. 7, 2004

(87) PCT Pub. No.: WO03/077191

PCT Pub. Date: Sep. 18, 2003

(65) Prior Publication Data

US 2005/0104457 A1    May 19, 2005

(30) Foreign Application Priority Data

Mar. 8, 2002  (EP) .................................. 02251653

(51) Int. Cl.
*A61F 2/00*  (2006.01)
(52) U.S. Cl. ..................... 600/30; 606/157; 128/903
(58) Field of Classification Search ............ 600/29–32; 128/903, DIG. 25; 607/60; 606/151, 153, 606/157, 158
See application file for complete search history.

(56) References Cited

U.S. PATENT DOCUMENTS

| | | | |
|---|---|---|---|
| 6,067,991 A | 5/2000 | Forsell | |
| 6,210,345 B1 | 4/2001 | Van Brunt | |
| 6,450,946 B1 | 9/2002 | Forsell | |
| 6,453,907 B1 | 9/2002 | Forsell | |
| 6,454,699 B1 | 9/2002 | Forsell | |
| 6,461,293 B1 | 10/2002 | Forsell | |
| 6,527,701 B1 * | 3/2003 | Sayet et al. | 600/30 |
| 6,547,801 B1 * | 4/2003 | Dargent et al. | 606/157 |
| 6,889,086 B2 * | 5/2005 | Mass et al. | 607/60 |
| 7,017,583 B2 | 3/2006 | Forsell | |
| 2005/0143765 A1 * | 6/2005 | Bachmann et al. | 606/157 |
| 2005/0143766 A1 * | 6/2005 | Bachmann et al. | 606/158 |

FOREIGN PATENT DOCUMENTS

| | | |
|---|---|---|
| DE | 100 20 688 | 12/2000 |
| EP | 0 695 558 | 2/1996 |
| WO | 89/11701 | 11/1989 |
| WO | WO 89/11701 | 11/1989 |
| WO | 00/66196 | 11/2000 |

OTHER PUBLICATIONS

U.S. Appl. No. 10/253,608, filed Sep. 25, 2002, Forsell, P.

\* cited by examiner

*Primary Examiner*—John P. Lacyk
(74) *Attorney, Agent, or Firm*—Franco A. Serafini; Luce, Forward, Hamilton & Scripps LLP

(57) ABSTRACT

An implantable device comprising: a stepper motor; a moveable member, moveable by the stepper motor; and an oscillator, wherein the oscillator is influenced by a signal derived from or supplied to the stepper motor to enable information on the moveable member to be fedback to an external controller by passive telemetry.

19 Claims, 3 Drawing Sheets

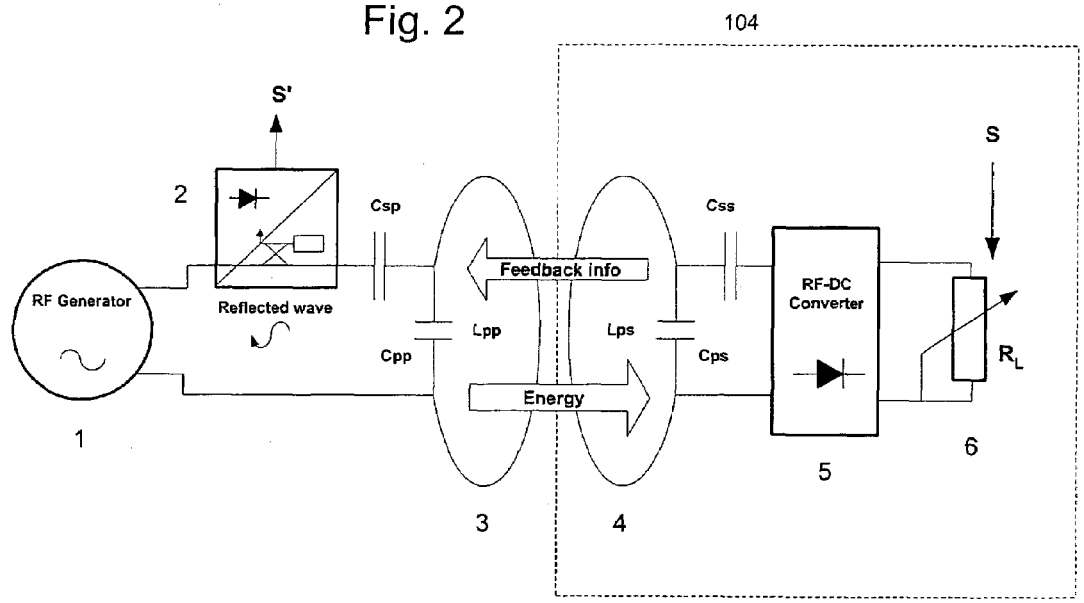
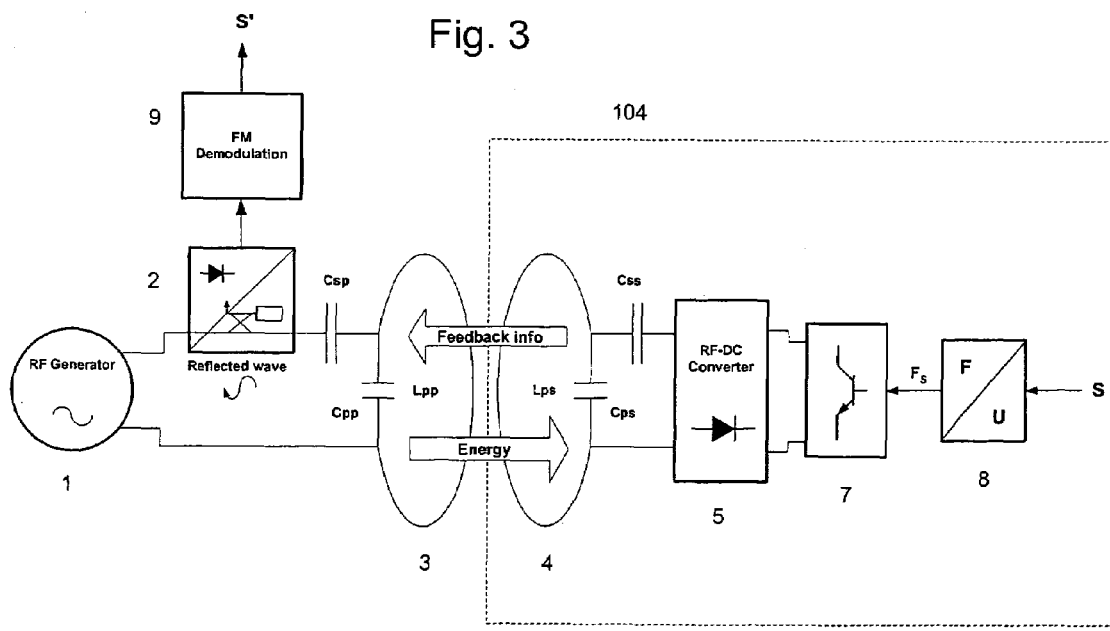

IMPLANTABLE DEVICE

The present invention relates to an implantable device comprising a moveable member for use in medical control and/or regulation.

Various types of long-term medical implantable devices using an actuator have been developed over the years, such as drug delivery pumps or regulation devices for the treatment of obesity of urinary incontinence. These devices are required to perform a specific action, for example delivery systems have to diffuse a drug at a precise location in the body and regulation devices have to apply greater or lesser degrees of constriction to an organ or a vessel. The actuator typically comprises a driving unit for providing motive force, and a movable member driven by the driving unit to perform the action. A number of different physical principles have been employed in such actuators, depending on the type of action, for example:

electromagnetic force—used by all types of electric motors used in peristaltic pumps or in valves;

pneumatic force—in drug delivery systems a pressurised gas pushes a compressible medication reservoir to expel the drug through a specific fluidic resistance; and hydraulic force—in regulation devices, constriction is achieved by an annular balloon filled with a physiologically acceptable solution.

It is also necessary for the action to be precisely controlled and the users need to be confidant that the action is correctly performed. Different types of action control are known:

Firstly the control can be performed autonomously by the device itself, and this may be either active or passive. An example of active control is where the control is electronic and performed by a microprocessor. In programmable infusion devices a peristaltic pump is driven by a microprocessor which controls the number of electrical pulses delivered to the pump. All the activity of the pump is recorded in a memory and the patient can access the data and change the pump parameters by radio frequency (RF) communication with an external control unit. An example of passive control is in some drug delivery devices which use pressurised gas to compress a medicament reservoir, the stability of the flow is determined by the design of the output fluidic resistance. The device is tested and calibrated for different types of drugs during the manufacturing process.

Secondly the control may be done by using an external diagnostic system, such as an Echo-Doppler for flow measurement or an angiography system to check the restriction size of a gastric banding.

There are a number of problems and drawbacks with the above existing implanted actuator technologies:

In programmable infusion pumps, the motor is powered by battery. The battery has a finite lifetime which means it needs to be changed, which involves additional surgery. The encapsulation of the battery also has to be perfect to avoid harmful leaks and diffusion. If there is a failure with the electronics, the pump could start on its own, because electric power is available in the device.

In infusion pumps with passive fluidic regulation, flow rate is affected by changes in altitude and/or temperature. The viscosity of the infusion solution, as well as the arterial pressure at the location of the catheter tip in vascular applications, can also affect flow rate.

In gastric regulation devices, an access port is located subcutaneously to regulate the amount of liquid in the hydraulic circuit. This regulation can be done only by puncture through a silicone membrane. This means that there are risks of infection and leakage.

Typically there is no direct feedback on whether the function to be achieved by the actuator has been fulfilled. The only way to get this information is indirectly, for example by measurements of the effects e.g. using an external diagnostic system.

To alleviate some of these problems there have been proposals to transmit energy to an implanted device using RF waves. There has also been proposed a method of getting data back from an implanted device known as "passive telemetry by absorbtion modulation" devised by Dr. P. A. Neukomm in the late 1980s, see for example CH 676164, WO 89/11701, EP 0377695 and the article *Passive Wireless Actuator Control and Sensor Signal Transmission*, Sensors and Actuators, A21-A23 (1990), 258-262. According to this method there is no need for an RF emitter in the implanted device, which means that no battery is used in the implant.

However, there are still a number of existing problems, such as the complexity and additional components needed to detect the status of the actuator, convert this to a signal for feedback and to achieve the desired modulation.

It is an object of the present invention to alleviate, at least partially, some or all of the problems previously described.

Accordingly the present invention provides an implantable device comprising:

a stepper motor;

a moveable member, moveable by the stepper motor; and an oscillator, wherein the oscillator is influenced by a signal derived from or supplied to the stepper motor to enable information on the moveable member to be fedback to an external controller by passive telemetry.

Using the signal derived from or supplied to the stepper motor to influence the oscillator means that the feedback of information can be done directly without requiring processing by a microprocessor in the implant. The use of a stepper motor is particularly advantageous because of the simplicity of the supply circuitry and because the signals applied to its coils are directly related to the displacement of the movable member; the displacement is proportional to the number of pulses given to the motor coils. Therefore it is not necessary to add shaft encoders or sensors to determine the status of the actuator.

Preferably the signal is the electrical signal applied to one coil of the stepper motor, or alternatively the signal is the voltage induced in a secondary coil wrapped around a coil of the stepper motor.

Preferably the signal modifies the frequency of the oscillator. For example, where the oscillator is a voltage controlled oscillator (VCO), this can be done directly, thereby eliminating the need for additional components and modulation means.

Preferably the device further comprises a microcontroller for driving the stepper motor, wherein the oscillator also comprises the external oscillator for providing a clock signal to the microcontroller. By using the external oscillator of the microcontroller as part of the oscillator for performing the modulation of the feedback signal, no additional components are necessary, and in particular it is not necessary to provide two dedicated oscillators.

Preferably a detector is provided to detect a reference position of the movable member and to influence the oscillator accordingly, preferably by causing a frequency shift of the oscillator. In this way, a small imprecision, such as an offset, in the calculated position of the movable member can be corrected.

The present invention also provides a system comprising: an implantable device as defined above; and an external controller comprising means for counting pulses in said signal fed back by passive telemetry to determine the motion of the stepper motor and the position of the movable member. The number of pulses in the signal contains information on the number of steps done by the rotor, and therefore provides an easy and precise way for determining the position of the movable member.

Preferably the external controller further comprises means for analysing the shape of the feedback signal to detect blockage of the stepper motor. Even if pulses are applied to the coils of the stepper motor, if the stepper motor cannot move because of a blockage, for example something obstructing the movable member, the rotor of the stepper motor will not turn and the magnetic circuit is disturbed. Consequently, by induction, the shape of the feedback signal is affected and such perturbations of the signal shape can be detected by the external controller.

Preferably the device or system described above further comprises one selected from the group consisting of:

a flow controller adjustable by said moveable member for blood flow regulation on native vessels or artificial grafts;

gastric banding adjustable by said moveable member for treatment of obesity;

oesophageal banding adjustable by said moveable member for treatment of Gastro Enteral Reflux Disease;

an artificial sphincter adjustable by said moveable member for treatment of urinary incontinence;

an artificial sphincter adjustable by said moveable member for treatment of faecal incontinence;

an artificial sphincter adjustable by said moveable member for use following a colostomy;

an artificial sphincter adjustable by said moveable member for use following an ileostomy; and a drug infusion system adjustable by said moveable member.

The present invention also provides use of a device or system as defined above in the manufacture of a medical device for use in at least one selected from the group of:

blood flow regulation on native vessels or artificial grafts;

gastric banding for treatment of obesity;

oesophageal banding for treatment of Gastro Enteral Reflux Disease;

control of an artificial sphincter for treatment of urinary incontinence;

control of an artificial sphincter for treatment of faecal incontinence;

control of an artificial sphincter following a colostomy;

control of an artificial sphincter following an ileostomy; and control of a drug infusion system.

The present invention also provides use of a device or system defined above in an application selected from the group consisting of:

blood flow regulation on native vessels or artificial grafts;

gastric banding for treatment of obesity;

oesophageal banding for treatment of Gastro Enteral Reflux Disease;

control of an artificial sphincter for treatment of urinary incontinence;

control of an artificial sphincter for treatment of faecal incontinence;

control of an artificial sphincter following a colostomy;

control of an artificial sphincter following an ileostomy; and control of a drug infusion system.

Embodiments of the invention will now be described, by way of example only, with reference to the accompanying drawings in which:

FIG. 2 is a block diagram of a passive telemetry system using the principle of absorption modulation;

FIG. 3 is a block diagram of a passive telemetry system using the principle of FM-AM absorption modulation.

In the figures, like reference numerals are used to identify like items.

Some principles of passive telemetry will firstly be explained to assist understanding of the present invention.

Figure 1:
FIG. 1 is a schematic illustration of a passive telemetry system comprising a wireless powered implanted device and external controller.

FIG. 1 shows the basic system used by the invention comprising an external controller 100 connected to an external antenna loop 102, and an implantable device 104 implanted beneath the skin 106 of the patient. The device 104 includes a receiving antenna, control electronics and an actuator. The external controller 100 delivers RF energy to the external antenna loop 102 which is transmitted to the implanted device to power its electronics and actuator. The external controller 100 also demodulates feedback information from the implantable device 104.

Referring to FIGS. 2 and 3, in the external controller, an RF generator 1 produces a forward-flowing wave at a carrier frequency $f_c$, for instance 27 MHz. The external loop antenna 3 emits mainly a magnetic field which is coupled into the implanted loop antenna 4. The antennas 3, 4 have inductancies $L_{pp}$ and $L_{ps}$, and are tuned with capacitors $C_{sp}$, $C_{pp}$ and $C_{ps}$, $C_{ss}$ in order to have high efficiency in RF power transmission. This efficiency depends on the resonance frequency of the antennas and on the impedance matching between the emitter and the receiver. The RF energy is then converted into DC electrical energy by the RF-DC converter 5 and the DC energy is used to supply the electronics, actuator and so on in the implanted device 104, which in FIG. 2 this is represented by the load $R_L$ 6. Working instructions can be superimposed on the RF signal by amplitude modulation (AM).

The maximum transmission distance between the antennas 3, 4 depends on their diameters, for example it might be in the region of 4 cm for the case of an external loop antenna 3 of diameter 6 cm and an implanted loop antenna 4 of 2 cm diameter.

The passive telemetry for feedback of information from the implanted device 104 to the external controller is carried out on the same RF fields as that which transfers energy to the implanted device, by modulation of the absorption rate within the implanted device. The principle is based on detuning of the coupled antennas 3, 4. The signal S to be transmitted back is used to vary the load within the implanted device 104 supplied by the RF-DC converter 5, so that a changing amount of RF energy is absorbed. The matching of the antennas 3, 4 varies at the same time, therefore the amplitude of the reflected wave changes in the external controller. By decoding the reflected wave, a signal S', proportional to the signal S can be extracted back in the external controller. Two different methods of coding the signal S exist:

1. Amplitude modulation (AM) of the reflected wave. As illustrated in FIG. 2, the signal S directly influences the load $R_L$ 6 such that the energy absorption rate is proportional to S and the amplitude of the reflected wave contains the information on signal S. In the external controller, the directional coupler 2 separates out the reflected wave to obtain the signal S' which is proportional to desired signal S. This method is simple, but is sensitive to any variation in the quality of coupling between the antennas 3, 4.

2. Modulation of the frequency of the amplitude modulation (FM-AM). As shown in FIG. 3, the signal S is applied to a voltage contolled oscillator (VCO) 8 such that the signal S is converted linearly into an oscillating signal at the frequency Fs, where Fs equals kxS. The signal Fs drives a switch 7 such that during the ON state of the switch 7 there is an increase in energy absorption from the RF-DC converter 5. Therefore the absorption rate is modulated at the frequency Fs and thus the frequency of the amplitude modulation of the reflected wave contains the information on the signal S. In the external controller, the directional coupler 2 separates the reflected wave where it can be decoded by FM demodulation in the demodulator 9 to obtain the signal S'. This method allows the transmission of different signals carried at different frequencies. It also has the advantage that the ON state of the switch can be very short and the absorption very strong without inducing an increase in average consumption and therefore the feedback transmission is less sensitive to variation in the quality of coupling between the antennas 3, 4.

Figure 4:
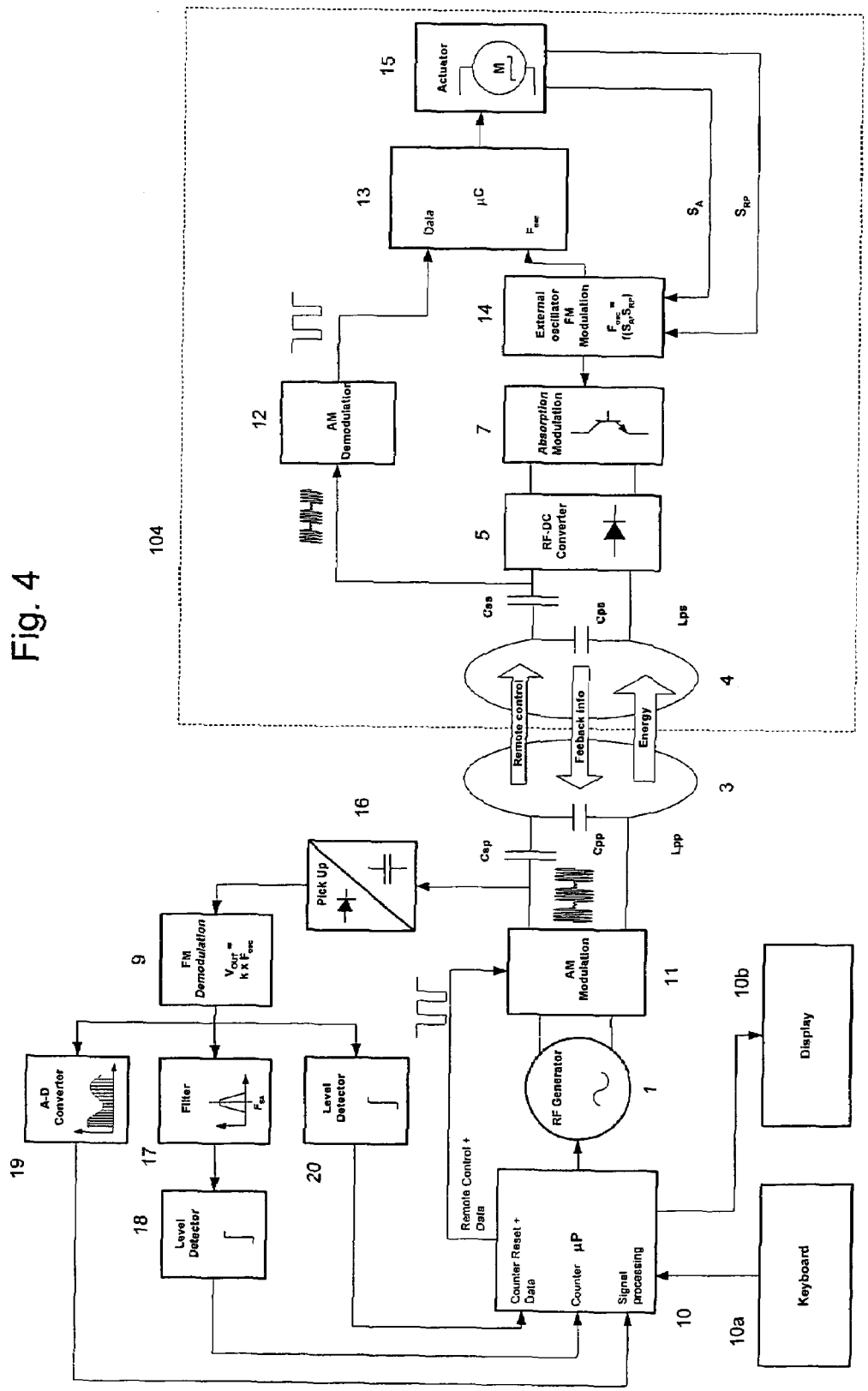
FIG. 4 is a block diagram of a passive telemetry system embodying the present invention.

The presently preferred embodiment of the invention is illustrated schematically in FIG. 4 and uses the principle of passive telemetry by FM-AM absorption modulation. The external controller on the left hand portion of FIG. 4 includes a microprocessor 10 with a user interface comprising a keyboard 10a and display 10b, which produces a signal comprising one or more data bytes to be transmitted to the implantable device 104. FIG. 4 explicitly shows a modulator 11 for amplitude modulation of the RF wave from the RF generator 1 which is emitted by the antenna 3. The emitted wave is received by the antenna 4 in the implantable device 104 and the AM demodulator 12 extracts the data bytes from the envelope of the RF signal and they are decoded and written into an EEPROM of the micro controller 13. A special code is used which allows an easy decoding by the micro controller, but also provides maximal security against communication failure. The micro controller 13 is provided with an external oscillator 14 for providing a clock signal to the micro controller 13. Various different embodiments exist for the external oscillator 14, for example:

A relaxation oscillator consisting of an external resistor-capacitor network connected to a discharging logic circuitry already implemented in the micro controller. This simple solution with only two additional components is suitable when the stability of the frequency is not so important. Another advantage is low current consumption.

A crystal oscillator consisting of a resonant circuit with a crystal, capacitors and logic circuits. This solution is preferable when a stable frequency is needed, but the number of external additional components and the current consumption are greater.

In the present invention the embodiment of the oscillator with external RC network is preferable, because of its simplicity.

The micro controller 13 interprets the received instructions to produce an output for driving the actuator 15, for example to produce motion in a particular direction by a particular amount. The actuator 15 comprises a bi-directional stepper motor and a movable member, movable by the stepper motor. A stepper motor is very suitable for use in an implantable device 104 because of its small thickness, typically 2 mm, its low power consumption, typically 25 mW, and its output torque after reduction gearings, typically 3 mNm. The stepper motor can produce very precise movement of the movable member, and depending on the particular application, this may be either rotational or axial movement, such that the mechanical output of the actuator is either a rotational torque or an axial force.

The stepper motor of the actuator 15 does not require complicated supply circuitry. Its two coils are directly connected to the micro controller 13, which receives the working instructions from the demodulator 12, interprets them and provides the voltage sequences to the coils. When the supply of voltage pulses to the stepper motor stops, all gearings stay in their position, even if a reverse torque or force is applied to the movable member of the actuator 15.

Using the stepper motor of the actuator 15 it is possible to obtain information on the movable member without adding sensors or encoders, because the displacement is proportional to the number of pulses given to the stepper motor coils. Two signals ensure precise control:

1. $S_A$, the actuator signal. According to one embodiment, this signal $S_A$ is the voltage signal taken at one of the outputs of the micro controller 13 connected to the motor coils. According to another embodiment, this signal $S_A$ is the induced voltage on a secondary coil wrapped around one motor coil of the actuator 15. In either case, this pulsating signal contains the information of the number of steps done by the rotor and also the indication of a blockage of the mechanism. If the rotor of the stepper motor does not turn, the magnetic circuit is disturbed, and by induction, it affects the signal $S_A$, for example altering the shape of the signal $S_A$. This can be detected in the external controller, as will be described later. The signal $S_A$ could equally be derived from the current applied to a motor coil instead of the voltage.

2. $S_{RP}$, the reference position signal. The actuator 15 includes a detector, such as an electrical contact switch, a Hall-effect switch, a force-sensing resistor, a variable inductor, or a piezoresistive element, which is activated when the movable member of the actuator reaches a reference position. This information can also be used by the external controller, as will be described below.

The signals $S_A$ and $S_{RP}$ are converted into frequencies through the external oscillator 14 which is a voltage controlled oscillator (VCO). The voltage level of the signal $S_A$ is applied to the external oscillator 14 to vary its frequency $F_{osc}$ proportionally to the signal $S_A$. Thus $F_{osc}$ contains all the information of $S_A$. When the movable member is hash at the reference position, the detector described above is activated to produce the reference position signal $S_{RP}$ which is used to induce a constant shift of the frequency $F_{osc}$, which shift is easily distinguishable from the variations due to signals $S_A$. If a relaxation oscillator is used as oscillator 14, the signals $S_A$ and $S_{RP}$ modify the charging current of the external resistor capacitor network. Preferably, the relaxation oscillator consists of an external resistor-capacitor network connected to a transistor and a logic circuit implemented in the micro controller circuitry. With $S_A$ and $S_{RP}$, the goal is to modify the charging current of the capacitor of the RC network in order to change the frequency of the relaxation oscillator. If the charging current is low, the voltage of the capacitor increases slowly and when the threshold of the transistor is reached, the capacitor discharges through the transistor. The frequency of the charging-discharging sequence depends on the charging current. If a crystal oscillator is used as oscillator 14, $S_A$ and $S_{RP}$ modify the capacitor of the resonant circuit. Preferably the crystal oscillator circuit consists of a crystal in parallel with capacitors. The crystal and capacitors form a resonant circuit which oscillates at a fixed frequency. This frequency can be adjusted by changing the capacitors. If one of these capacitors is a Varicap (kind of diode), it is possible to vary its capacitance value by modifying the reverse voltage applied on it. $S_A$ and $S_{RP}$ can be used to modify this voltage.

Hence, the signals $S_A$ and $S_{RP}$, are used to modify at least one parameter of a resistor-capacitor (RC) network associated with the oscillator 14 or at least one parameter of a crystal oscillator comprising the oscillator 14.

As can be seen in FIG. 4, the signals $S_A$ and $S_{RP}$, derived from the stepper motor or from the output of the microcontroller 13, can be used directly for frequency modulation by the VCO 14 without any encoding or intervention by the microcontroller 13. By using the external oscillator 14 of the micro controller 13 as part of the VCO for the feedback signal, no additional components have to be added, and the operation of the micro controller 13 is not adversely affected by the changes in the oscillator frequency $F_{osc}$. The oscillating signal $F_{osc}$ drives the voltage driven switch 7 for absorption modulation, such that feedback transmission is performed with passive telemetry by FM-AM absorption modulation, as previously described.

In the external controller, the feedback signal $F_{osc}$ is detected by the pickup 16 and fed to FM demodulator 9 which produces a voltage output $V_{OUT}$ which is proportional to $F_{osc}$. $V_{OUT}$ is fed to filter 17 and level detector 18 to obtain the information corresponding to the actuator signal $S_A$ which corresponds to the pulses applied to the stepper motor coil. The microprocessor 10 counts these pulses and calculates the corresponding displacement of the movable member of the actuator 15, which is proportional to the number of pulses. The signal $V_{OUT}$ is also passed through analogue-to-digital converter 19 and the digital output is fed to the microprocessor 10 where signal processing is performed to detect perturbations of the shape of the feedback signal which would indicate a blockage of the rotor of the stepper motor which would indicate, for example, an obstruction of the movable member. The microprocessor 10 would stop counting any detected motor pulses when it detected that the actuator was blocked, and would output an indication of this status. The level detector 20 produces an output when it detects that the demodulated signal $V_{OUT}$ indicates the presence of the reference position signal $S_R P$ due to activation of the reference position detector. This output induces a reset of the position of the movable member calculated by the microprocessor 10 in the external controller. In this way, a small imprecision, e.g. an offset, can be corrected.

As shown in FIG. 1, and by the dashed line in FIGS. 2, 3 and 4, the implantable device 104 contains all the electronics and the actuator encapsulated into a compact biocompatible plastic package, which allows good RF transmission to the internal antenna loop 4. However, according to alternative embodiments of the invention, the antenna loop 4 and/or the actuator 15 may be provided remotely from the rest of the device, for example to enable the antenna coil 4 to be nearer the skin of the patient for better transmission, or to enable the actuator 15 to be implanted at a deep location.

The device embodying the the invention described above can be used for any suitable application, in which the lumen of any bodily vessel or tube (native or artificial) should be adjusted, for example: blood flow regulation on native vessels or artificial grafts, gastric banding for treatment of obesity, oesophageal banding for treatment of GERD (Gastro Enteral Reflux Disease), control of an artificial sphincter for treatment of urinary incontinence, control of an artificial sphincter for treatment of faecal incontinence, control of an artificial sphincter following a colostomy, control of an artificial sphincter following an ileostomy. The technology is also suitable for use in drug infusion systems.

The invention claimed is:

1. An implantable device comprising:
a stepper motor;
a moveable member, moveable by the stepper motor; and
an intracorporeal oscillator,
wherein the intracorporeal oscillator is influenced by a signal directly derived from or supplied to the stepper motor to enable information on the moveable member to be fedback to an external controller by passive telemetry.

2. A device according to claim 1, wherein said signal is the electrical signal applied to one coil of the stepper motor.

3. A device according to claim 1, wherein said signal is the voltage induced in a secondary coil wrapped around a coil of the stepper motor.

4. A device according to claim 1, wherein the intracorporeal oscillator drives an absorption modulator for use in feedback of said information by passive telemetry using FM-AM modulation.

5. A device according to claim 1, wherein said signal modifies the frequency of the intracorporeal oscillator.

6. A device according to claim 5, wherein said signal is used to modify one of:
at least one parameter of a resistor-capacitor network associated with the intracorporeal oscillator; and
at least one parameter of a crystal oscillator comprising the intracorporeal oscillator.

7. A device according to claim 1, further comprising a microcontroller for driving the stepper; and
an intracorporeal oscillator external to the microcontroller, wherein the intracorporeal oscillator provides a clock signal to the microcontroller.

8. A device according to claim 1, wherein a reference position of the moveable member is detected by a detector which is used to influence the intracorporeal oscillator.

9. A device according to claim 8, wherein said detector causes a shift in frequency of said intracorporeal oscillator when the reference position is detected.

10. A device according to claim 8 wherein the detector is selected from the group consisting of: an electrical contact switch, a Hall-effect switch, a force-sensing resistor, a variable inductor, and a piezoresistive element.

11. A device according to claim 1, encapsulated into a biocompatible, non-metallic package.

12. A system comprising:
an implantable device according to claim 1, and
an external controller comprising means for counting pulses in said signal fedback by passive telemetry for determining the motion of the stepper motor and the position of the moveable member.

13. A system according to claim 12, wherein said external controller further comprises means for analyzing the shape of said signal to detect blockage of the stepper motor.

14. A device according to claim 1, wherein the moveable member is structured for constricting a passageway.

15. A method for operating an implantable device comprising:
providing the implantable device with a stepper motor, a moveable member moveable by the stepper motor, and an intracorporeal oscillator;
providing an external controller; and
causing the intracorporeal oscillator to be influenced by a signal directly derived from or supplied to the stepper motor, thereby enabling information on the moveable member to be fedback to the external controller by passive telemetry.

16. The method of claim 15, wherein causing the intracorporeal oscillator to be influenced by a signal directly derived from or supplied to the stepper motor comprises deriving the signal as the electrical signal applied to one coil of the stepper motor or as the voltage induced in a secondary coil wrapped around a coil of the stepper motor.

17. The method of claim 15, further comprising causing the intracorporeal oscillator to drive an absorption modulator providing feedback of the information by passive telemetry using FM-AM modulation.

18. The method of claim 15, wherein the frequency of the intracorporeal oscillator is modified by the signal.

19. The method of claim 1, wherein the intracorporeal oscillator is further influenced by a detector detecting a reference position of the moveable member.

* * * * *